United States Patent
Yamamoto et al.

[11] Patent Number: 6,111,115
[45] Date of Patent: Aug. 29, 2000

[54] PREPARATION OF 2-(10,11-DIHYDRO-10-OXODIBENZO-[B,F]THIEPIN-2-YL) PROPIONIC ACID

[75] Inventors: Masao Yamamoto; Kunio Kobayashi, both of Saitama; Katsumasa Harada, Yamaguchi; Shigeyoshi Nishino, Yamaguchi; Hiroshi Sasaki, Yamaguchi, all of Japan

[73] Assignees: Nippon Chemiphar Co., Ltd., Tokyo; Ube Industries, Ltd., Yamaguchi, both of Japan

[21] Appl. No.: 09/242,483

[22] PCT Filed: Aug. 22, 1997

[86] PCT No.: PCT/JP97/02922

§ 371 Date: Feb. 17, 1999

§ 102(e) Date: Feb. 17, 1999

[87] PCT Pub. No.: WO98/07717

PCT Pub. Date: Feb. 26, 1998

[30] Foreign Application Priority Data

Aug. 22, 1996 [JP] Japan .................................. 8-241088
Dec. 12, 1996 [JP] Japan .................................. 8-352799

[51] Int. Cl.$^7$ ...................... C07D 337/14; C07C 205/00; C07C 229/00

[52] U.S. Cl. .................................. 549/12; 560/9; 560/23; 560/44

[58] Field of Search ................... 549/12; 560/9, 560/23, 44

[56] References Cited

FOREIGN PATENT DOCUMENTS 55-53282 4/1980 Japan .
62-29780 12/1987 Japan .
63-10756 1/1988 Japan .

*Primary Examiner*—Amelia Owens
*Attorney, Agent, or Firm*—McAulay Nissen Goldberg & Kiel, LLP

[57] ABSTRACT

A process for preparation of 2-(10,11-dihydro-10-oxodibenzo[b,f]thiepin-2-yl)propionic acid (i.e., Zaltoprofen) is performed by subjecting 2-(4-amino-3-carboxy-methylphenyl)propionic acid or its salt to diazotization and subsequent reaction with thiophenol to produce 2-(3-carboxymethyl-4-phenylthiophenyl)propionic acid or its salt, and subjecting the product to cyclization reaction. Other related processes and related compounds are also disclosed.

24 Claims, No Drawings

PREPARATION OF 2-(10,11-DIHYDRO-10-OXODIBENZO-[B,F]THIEPIN-2-YL) PROPIONIC ACID

FIELD OF THE INVENTION

This invention relates to new processes for preparing "Zaltoprofen", i.e., 2-(10,11-dihydro-10-oxodibenzo-[b,f]thiepin-2-yl)propionic acid. The invention further relates to new compounds which are favorably employable for the processes for the preparation of Zaltoprofen.

BACKGROUND OF THE INVENTION

Zaltoprofen is known as a pharmaceutically active compound which shows excellent anti-inflammatory effect as well as excellent analgesic effect.

Japanese Patent Provisional Publication No. 55-53282 describes a process for preparing Zaltoprofen which comprises hydrolyzing ethyl 5-(α-cyanoethyl)-2-phenylthiophenylacetate to give 5-(α-cyanoethyl)-2-phenylthiophenylacetic acid, subjecting the resulting compound to cyclization and amidation of cyano group, and hydrolyzing the amide group of the resulting compound.

Japanese Patent Provisional Publication No. 57-106678 describes an improved process for preparing Zaltoprofen which comprises hydrolyzing ethyl 5-(α-cyanoethyl)-2-phenylthiophenylacetate to give 2-(3-carboxymethyl-4-phenylthiophenyl)propionic acid and cyclizing the resulting compound in the presence of a condensation agent.

Japanese Patent Provisional Publications No. 62-292780 and No. 63-10756 describe a process for preparing Zaltoprofen which starts from a haloketal compound.

Japanese Patent Provisional Publication No. 63-2970 describes a process for preparing Zaltoprofen in which methyl 5-propionyl-2-phenylthiophenylacetate is reacted with an orthoformic acid ester and metallic zinc or zinc halide to produce methyl 2-(3-methoxycarbonylmethyl-4-phenylthiophenyl)propionate, and this product is employed for the preparation of Zaltoprofen.

As described above, a variety of processes for preparing Zaltoprofen are known. However, more improved processes are desired from the viewpoints of availability of the starting materials and easy handling of the materials participating in the reactions for the preparation, as well as economical viewpoints such as yields.

The present invention has an object to provide new processes for preparing Zaltoprofen.

Specifically, the invention has an object to provide new processes for preparing Zaltoprofen which are advantageously employable in industry from the viewpoints of availability of the starting materials and easy handling of the materials participating in the reactions for the preparation, as well as economical viewpoints such as yields.

SUMMARY OF THE INVENTION

The present invention resides in a process for preparing 2-(10,11-dihydro-10-oxodibenzo[b,f]thiepin-2-yl)propionic acid which comprises subjecting 2-(4-amino-3-carboxymethylphenyl)propionic acid or its salt to diazotization and subsequent reaction with thiophenol to produce 2-(3-carboxymethyl-4-phenylthiophenyl)propionic acid or its salt, and subjecting the product to cyclization reaction—(Preparation-I).

The invention also resides in a process for preparing 2-(10,11-dihydro-10-oxodibenzo[b,f]thiepin-2-yl)propionic acid which comprises subjecting 2-(4-amino-3-carboxymethylphenyl)propionic acid or its salt to diazotization and subsequent reaction with a halogenating agent to produce 2-(3-carboxymethyl-4-halogenophenyl)propionic acid or its salt, causing a reaction of the product with thiophenol to produce 2-(3-carboxymethyl-4-phenylthiophenyl)propionic acid or its salt, and subjecting the product to cyclization reaction—(Preparation-II).

The invention further resides in a process for preparing 2-(10,11-dihydro-10-oxodibenzo[b,f]thiepin-2-yl)propionic acid which comprises subjecting 2-(4-amino-3-carboxymethylphenyl)propionic acid or its salt to diazotization and subsequent reaction with thiosalicylic acid to produce 2-[3-carboxymethyl-4-(2-carboxyphenylthio)phenyl] propionic acid or its salt, esterifying the product to give a 2-[3-(lower)alkoxycarbonylmethyl-4-(2-(lower)alkoxycarbonylphenylthio)phenyl]propionic acid (lower) alkyl ester, cyclizing the resulting ester to produce a 2-(10,11-dihydro-11-(lower)alkoxycarbonyl-10-oxodibenzo[b,f]thiepin-2-yl)propionic acid (lower)alkyl ester, and subjecting the resulting ester to hydrolysis and decarboxylation—(Preparation-III).

The invention furthermore resides in a process for preparing 2-(10,11-dihydro-10-oxodibenzo[b,f]thiepin-2-yl)propionic acid which comprises subjecting 2-(4-amino-3-carboxymethylphenyl)propionic acid or its salt to diazotization and subsequent reaction with a halogenating agent to produce 2-(3-carboxymethyl-4-halogenophenyl)propionic acid or its salt, causing a reaction of the product with thiosalicylic acid to produce 2-[3-carboxymethyl-4-(2-carboxyphenylrhio)phenyl]propionic acid or its salt, esterifying the product to give a 2-[3-(lower)alkoxycarbonylmethyl-4-(2-(lower)alkoxycarbonylphenylthio)phenyl]propionic acid (lower) alkyl ester, cyclizing the resulting ester to produce a 2-(10,11-dihydro-11-(lower)alkoxycarbonyl-10-oxodibenzo[b,f]thiepin-2-yl)propionic acid (lower)alkyl ester, and subjecting the resulting ester to hydrolysis and decarboxylation—(Preparation-IV).

The 2-(4-amino-3-carboxymethylphenyl)propionic acid or its salt is a new compound, and it can be produced by a variety of processes described below.

1) A process which comprises reducing 2-(3-carboxymethyl-4-nitrophenyl)propionic acid or its salt.

2) A process which comprises subjecting a methylmalonic acid derivative of the following formula (A):

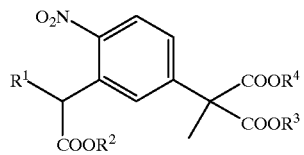

in which $R^1$ represents cyano, carboxyl, carbamoyl, alkylcarbonyl having 2 to 7 carbon atoms, alkoxycarbonyl having 2 to 7 carbon atoms, aryloxycarbonyl having 7 to 13 carbon atoms, or aralkyloxycarbonyl having 8 to 19 carbon atoms; and each of $R^2$, $R^3$ and $R^4$ independently represents hydrogen, alkyl having 1 to 6 carbon atoms, aryl having 6 to 12 carbon atoms, or aralkyl having 7 to 18 carbon atoms to hydrolysis and decarboxylation, to produce 2-(3-carboxymethyl-4-nitrophenyl)propionic acid or its salt, and reducing the product.

3) A process which comprises causing a reaction of an acetic acid ester derivative with a 2-(3-halogeno-4- nitrophenyl)-2-methylmalonic acid dialkyl ester[=2-(3-halogeno-4-nitrophenyl)-2-methylpropanedioic acid dialkyl ester], to give a methylmalonic acid derivative of the abovementioned formula (A); subjecting the methylmalonic acid derivative to hydrolysis and decarboxylation, to produce 2-(3-carboxymethyl-4-nitrophenyl)propionic acid or its salt; and reducing the product.

4) A process which comprises causing successive reactions of a 2,4-dihalogenonitrobenzene with a methylmalonic acid diester and with an acetic acid ester derivative, to give a methylmalonic acid derivative of the aforementioned formula (A); subjecting the methylmalonic acid derivative to hydrolysis and decarboxylation, to produce 2-(3-carboxymethyl-4-nitrophenyl)propionic acid or its salt; and reducing the product.

5) A process which comprises reducing a methylmalonic acid derivative of the aforementioned formula (A), to give another methylmalonic acid derivative having the following formula (B):

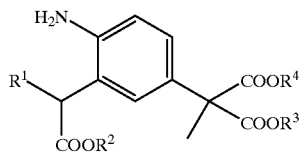

in which each of $R^1$, $R^2$, $R^3$ and $R^4$ has the meaning as defined above for the formula (A); and subjecting the methylmalonic acid derivative of the formula (B) to hydrolysis and decarboxylation.

The invention furthermore resides in a process for preparing 2-(10,11-dihydro-10-oxodibenzo[b,f]thiepin-2-yl)propionic acid which comprises causing a reaction of 2-(3-carboxymethyl-4-halogenophenyl)propionic acid or its salt with thiophenol, to produce 2-(3-carboxymethyl-4-phenylthiophenyl)propionic acid or its salt, and cyclizing the product—(Preparation-V).

The invention furthermore resides in a process for preparing 2-(10,11-dihydro-10-oxodibenzo[b,f]thiepin-2-yl)propionic acid which comprises causing a reaction of 2-(3-carboxymethyl-4-halogenophenyl)propionic acid or its salt with thiosalicylic acid, to produce 2-[3-carboxymethyl-4-(2-carboxyphenylthio)phenyl]propionic acid or its salt, esterifying the product to give a 2-[3-(lower)alkoxycarbonylmethyl-4-(2-(lower)alkoxycarbonylphenylthio)phenyl]propionic acid (lower) alkyl ester, cyclizing the resulting ester, and subjecting the cyclized ester to hydrolysis and decarboxylation—(Preparation-VI).

Furthermore, the invention resides in a compound having the following formula (C):

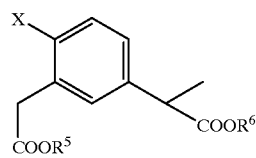

in which X represents $NO_2$, $NH_2$, halogen, or a group of the following formula:

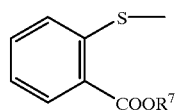

in which $R^7$ represents hydrogen, alkyl having 1 to 6 carbon atoms, aryl having 6 to 12 carbon atoms, or aralkyl having 7 to 18 carbon atoms, and each of $R^5$ and $R^6$ independently represents hydrogen, alkyl having 1 to 6 carbon atoms, aryl having 6 to 12 carbon atoms, or aralkyl having 7 to 18 carbon atoms.

The compound of the formula (C) is of value as an intermediate compound for preparing the 2-(10,11-dihydro-10-oxodibenzo[b,f]thiepin-2-yl)propionic acid.

Representative examples of the compounds of the formula (C) include the following:

a) 2-(3-Carboxymethyl-4-nitrophenyl)propionic acid, its alkyl ester in which the alkyl has 1 to 6 carbon atoms, or its salt.

b) 2-(4-Amino-3-carboxymethylphenyl)propionic acid, its alkyl ester in which the alkyl has 1 to 6 carbon atoms, or its salt.

c) 2-[3-Carboxymethyl-4-(2-carboxyphenylthio)phenyl]propionic acid, its alkyl ester in which the alkyl has 1 to 6 carbon atoms, or its salt.

d) 2-(3-Carboxymethyl-4-halogenophenyl)propionic acid, its alkyl ester in which the alkyl has 1 to 6 carbon atoms, or its sale.

e) An alkyl ester of 2-[3-alkoxycarbonylmethyl-4-(2-alkoxycarbonylphenylthio)phenyl]propionic acid in which the alkyl has 1 to 6 carbon atoms and the alkoxy has 1 to 6 carbon atoms.

Furthermore, the invention resides in a compound having the following formula (D):

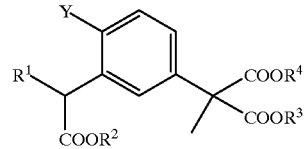

in which Y represents $NO_2$ or $NH_2$, $R^1$ represents cyano, carboxyl, carbamoyl, alkylcarbonyl having 2 to 7 carbon atoms, alkoxycarbonyl having 2 to 7 carbon atoms, aryloxycarbonyl having 7 to 13 carbon atoms, or aralkyloxycarbonyl having 8 to 19 carbon atoms; and each of $R^2$, $R^3$ and $R^4$ independently represents hydrogen, alkyl having 1 to 6 carbon atoms, aryl having 6 to 12 carbon atoms, or aralkyl having 7 to 18 carbon atoms.

The compound of the formula (D) also is of value as an intermediate compound for preparing the 2-(10,11-dihydro-10-oxodibenzo[b,f]thiepin-2-yl)propionic acid.

Representative examples of the compounds of the formula (D) include the following:

a) Dialkyl ester of 2-[3-bis(alkoxycarbonyl)methyl-4-nitrophenyl]-2-methylmalonic acid in which the alkyl has 1 to 6 carbon atoms and the alkoxy has 1 to 6 carbon atoms.

b) Dialkyl ester of 2-[3-[(alkoxycarbonyl)cyanomethyl]-4-nitrophenyl]-2-methylmalonic acid in which the alkyl has 1 to 6 carbon atoms and the alkoxy has 1 to 6 carbon atoms.

c) Dialkyl ester of 2-[3-[acetyl(alkoxycarbonyl)methyl]-4-nitrophenyl]-2-methylmalonic acid in which the alkyl has 1 to 6 carbon atoms and the alkyoxy has 1 to 6 carbon atoms.

d) Dialkyl ester of 2-[4-amino-3-bis(alkoxycarbonyl)methylphenyl]-2-methylmalonate in which the alkyl has 1 to 6 carbon atoms and the alkoxy has 1 to 6 carbon atoms.

Furthermore, the invention resides in a compound having the following formula (E):

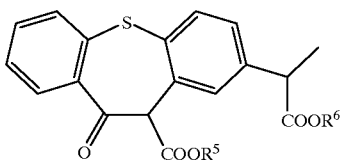

in which each of $R^5$ and $R^6$ independently represents hydrogen, alkyl having 1 to 6 carbon atoms, aryl having 6 to 12 carbon atoms, or aralkyl having 7 to 18 carbon atoms.

The compound of the formula (E) also is of value as an intermediate compound for preparing the 2-(10,11-dihydro-10-oxodibenzo[b,f]thiepin-2-yl)propionic acid.

Representative examples of the compounds of the formula (E) include an alkyl ester of 2-(11-alkoxycarbonyl-10,11-dihydro-10-oxodibenxo[b,f]thiepin-2-yl)propionic acid in which the alkyl has 1 to 6 carbon atoms and the alkoxy has 1 to 6 carbon atoms.

PREFERRED EMBODIMENTS OF THE INVENTION

The processes of the invention for preparing Zaltoprofen, that is, 2-(10,11-dihydro-10-oxodibenzo-[b,f]thiepin-2-yl)propionic acid, are further described below in more detail.

(1) Preparation-I

Preparation-I of the invention for preparing Zaltoprofen is characterized in that 2-(4-amino-3-carboxymethylphenyl)propionic acid or its salt is diazotized and then reacted with thiophenol to give 2-(3-carboxymethyl-4-phenylthiophenyl)propionic acid or its salt, and the resulting product is then subjected to cyclization reaction. Preparation-I is illustrated in the following reaction scheme I:

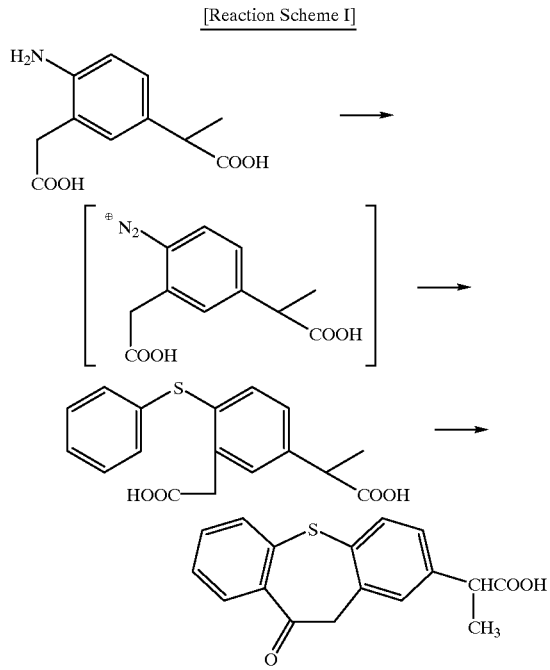

[Reaction Scheme I]

1) Preparation of 2-(3-carboxymethyl-4-phenylthiophenyl) propionic acid or its salt 2-(4-Amino-3-carboxymethylphenyl)propionic acid or its salt (e.g., disodium salt, dipotassium salt, di-lithium salt) is diazotized by the use of a diazotizing agent, for instance, under acidic conditions (made acidic with hydrochloric acid), and the resulting compound (i.e., diazo compound) is reacted with thiophenol in a solvent. The diazotization reaction can be performed by bringing the starting compound into contact with a diazotizing agent (e.g., sodium nitrite, nitrosyl hydrogensulfate, nitrosyl chloride) at −10 to 20° C. under acidic conditions (made acidic with hydrochloric acid, sulfuric acid, or acetic acid). The resulting compound (i.e., diazo compound) is then brought into contact with thiophenol at 0 to 100° C. under basic conditions (e.g., in an aqueous sodium hydroxide or potassium hydroxide solution) to give the 2-(3-carboxymethyl-4-phenylthiophenyl)propionic acid or its salt.

2) Preparation of Zaltoprofen

The above-mentioned 2-(3-carboxymethyl-4-phenylthiophenyl)propionic acid or its salt is a known compound. The preparation of Zaltoprofen by cyclizing this compound in the presence of a condensation agent is described in Japanese Patent Publication H1-29793. The condensation agent can be sulfuric acid, polyphosphoric acid, or polyphosphoric acid ester, and the reaction is generally performed at a temperature of 0 to 150° C.

(2) Preparation-II and Preparation-V

Preparation-II of the invention for preparing Zaltoprofen is characterized in that 2-(4-amino-3-carboxymethylphenyl)propionic acid or its salt is diazotized and then reacted with a halogenating agent to give 2-(3-carboxymethyl-4-halogenophenyl)propionic acid or its salt, and the resulting compound is reacted with thiophenol to give 2-(3-carboxymethyl-4-phenylthiophenyl)propionic acid or its salt, which is finally subjected to cyclization reaction. Preparation-II is illustrated in the following reaction scheme II (in the scheme, "Hal-" means a halogeno group):

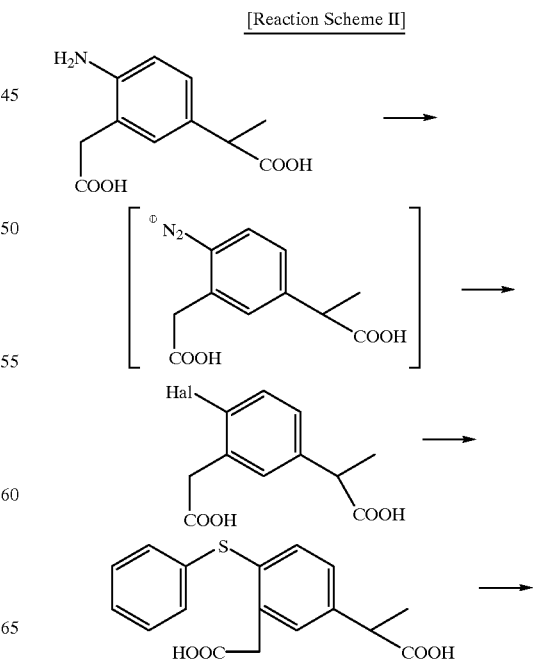

[Reaction Scheme II]

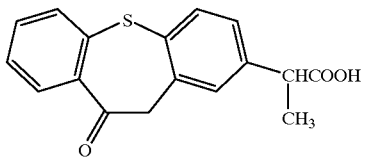

In Reaction Scheme II, the route in which 2-(3-carboxymethyl-4-halogenophenyl)propionic acid or its salt is reacted with thiophenol (not illustrated) to give 2-(3-carboxymethyl-4-phenylthiophenyl)propionic acid or its salt, and this product is cyclized to give Zaltoprofen (final product) corresponds to Preparation-V.

1) Preparation of 2-(3-carboxymethyl-4-halogenophenyl) propionic acid or its salt 2-(4-Amino-3-carboxymethylphenyl)propionic acid or its salt (e.g., disodium salt) is diazotized in the same manner as in Preparation-I, and the resulting compound (i.e., diazo compound) is treated with a halogenating agent (e.g., potassium iodide, copper(I) chloride, copper (I) bromide, copper (I) iodide, or hydrobromic acid generally in the presence of powdery copper) at −10 to 100° C., to give the 2-(3-carboxymethyl-4-halogenophenyl)propionic acid or its salt.

2) Preparation of 2-(3-carboxymethyl-4-phenylthiophenyl) propionic acid or its salt The above-mentioned 2-(3-carboxymethyl-4-halogenophenyl)propionic acid or its salt is reacted with thiophenol in a polar solvent (e.g., dimethylsulfoxide (DMSO), N,N-dimethylformamide (DMF), or water) at 25 to 120° C., under basic conditions (e.g., made basic with potassium hydroxide or potassium carbonate) in the presence of a catalyst (e.g., potassium iodide, powdery copper, copper salt), to give the 2-(3-carboxymethyl-4-phenylthiophenyl)propionic acid or its salt.

3) Preparation of Zaltoprofen

The process described in the aforementioned Preparation-I can be utilized.

(3) Preparation-III

Preparation-III of the invention for preparing Zaltoprofen is characterized in that 2-(4-amino-3-carboxymethylphenyl) propionic acid or its salt is diazotized and then reacted with thiosalicylic acid to give 2-[3-carboxymethyl-4-(2-carboxyphenylthio)phenyl]propionic acid or its salt; the resulting compound is esterified to give 2-[3-(lower)alkoxycarbonylmethyl-4-(2-(lower) alkoxycarbonylphenylthio)phenyl]propionic acid (lower) alkyl ester; the resulting ester is subjected to cyclization reaction, to give 2-(10,11-dihydro-11-(lower) alkoxycarbonyl-10-oxodibenzo[b,f]thiepin-2-yl)propionic acid (lower)alkyl ester; and the resulting ester is finally subjected to hydrolysis and decarboxylation. Preparation-III is illustrated in the following reaction scheme III:

[Reaction Scheme III]

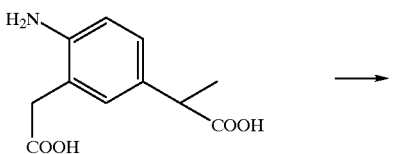

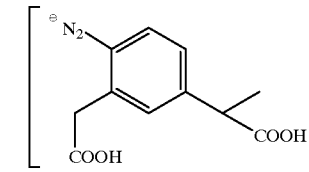

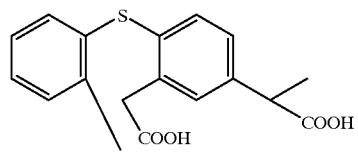

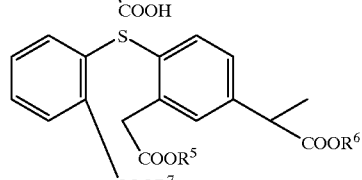

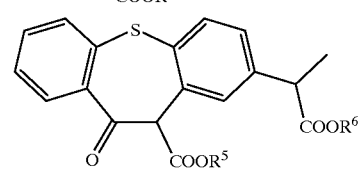

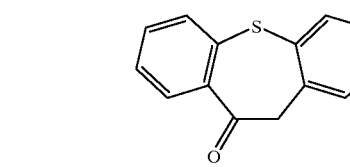

1) Preparation of 2-[3-carboxymethyl-4-(2-carboxyphenylthio)phenyl]propionic acid or its salt 2-(4-Amino-3-carboxymethylphenyl)propionic acid or its salt is diazotized in the same manner as in Preparation-I, and the resulting compound (i.e., diazo compound) is reacted with thiosalicylic acid at 0 to 100° C., preferably under basic conditions, to give the 2-[3-carboxymethyl-4-(2-carboxyphenylthio)phenyl]propionic acid or its salt.

2) Preparation of 2-[3-(lower)alkoxycarbonylmethyl-4-(2-(lower)alkoxycarbonylphenylthio)phenyl]propionic acid (lower)alkyl ester The esterification reaction can be performed by utilizing a lower alcohol (alcohol having 1 to 6 carbon atoms, such as methanol, ethanol, n-propanol or isopropanol), utilizing other esterifying agent (e.g., methyl orthoformate, or ethyl orthoformate), or utilizing both of the lower alcohol and other esterifying agent. In the esterification reaction, an inorganic acid such as sulfuric acid or hydrochloric acid, an organic acid such as an aromatic sulfonic acid, or a Lewis acid such as boron trifluoride etherate is preferably employed in a catalytic amount or more so that the reaction can be accelerated.

3) Preparation of 2-(10,11-dihydro-11-(lower) alkoxycarbonyl-10-oxodibenzo[b,f]thiepin-2-yl)propionic acid (lower)alkyl ester by cyclization of 2-[3-(lower) alkoxycarbonylmethyl-4-(2-(lower) alkoxycarbonylphenylthio)phenyl]propionic acid lower alkyl ester The cyclization reaction is known as Dieckmann reaction, and the compound to be cyclized is brought into contact with a base in a solvent. Examples of the bases include alkali metals (e.g., sodium metal), alcoholates of alkali metals (e.g., potassium tert-butoxide, and sodium methoxide), alkali metal hydrides (e.g., sodium hydride), and sodium methylsulfinylmethide. The solvent can be benzene, toluene, xylene, ethyl ether, or dimethylsulfoxide. The reaction temperature can be in the range of 0° C. to the boiling temperatue of the solvent.

4) Preparation of Zaltoprofen by hydrolysis and decarboxylation of 2-(10,11-dihydro-11-(lower)alkoxycarbonyl-10-oxodibenzo[b,f]thiepin-2-yl)propionic acid (lower)alkyl ester The hydrolysis and decarboxylation can be performed without isolating an intermediate product. For instance, the alkyl ester (starting compound) is placed in an aqueous hydrochloric or sulfuric acid solution (optionally, a lower aliphatic acid such as acetic acid or propionic acid can be incorporated), and heated to the reaction temperature in the range of from 500C to the boiling temperature of the solvent, whereby the desired hydrolysis and decarboxylation reaction can proceed.

(4) Preparation-IV and Preparation-VI

Preparation-IV of the invention for preparing Zaltoprofen is characterized in that 2-(4-amino-3-carboxymethylphenyl) propionic acid or its salt is diazotized and then reacted with a halogenating agent to give 2-(3-carboxymethyl-4-halogenophenyl)propionic acid or its salt; the resulting compound is reacted with thiosalicylic acid to give 2-[3-carboxymethyl-4-(2-carboxyphenylthio)phenyl]propionic acid or its salt; the product is then esterified to give 2-[3-(lower)alkoxycarbonylmethyl-4-(2-(lower)alkoxycarbonylphenylthio)phenyl]propionic acid (lower) alkyl ester; the resulting ester is subjected to cyclization reaction to give 2-(10,11-dihydro-11-(lower) alkoxycarbonyl-10-oxodibenzo[b,f]thiepin-2-yl)propionic acid (lower)alkyl ester; and finally the resulting ester is subjected to hydrolysis and decarboxylation. Preparation-IV is illustrated in the following Reaction Scheme IV (in the scheme, "Hal-" means a halogeno group):

[Reaction Scheme IV]

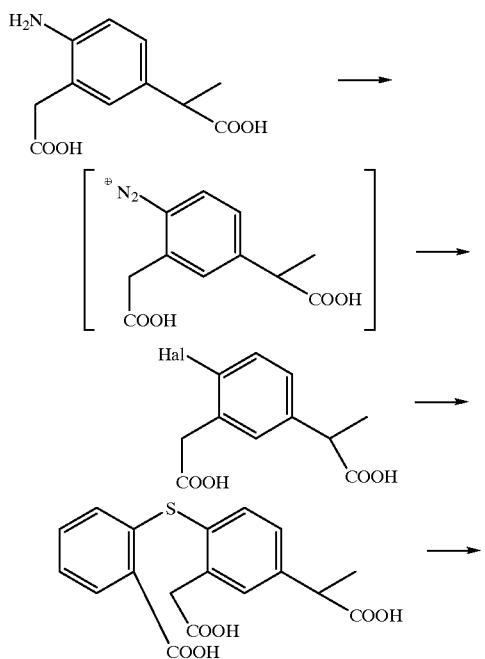

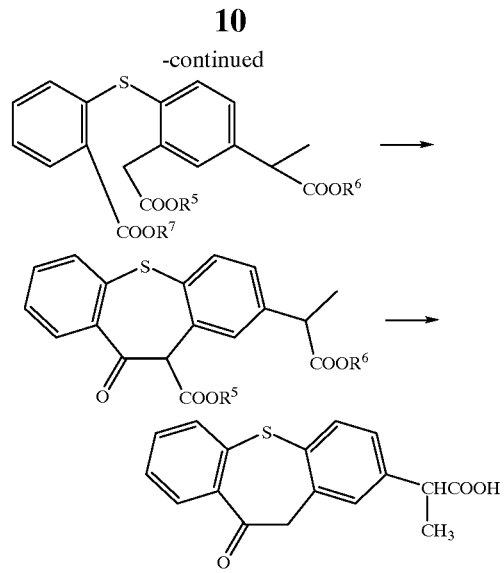

In Reaction Scheme IV, the route starting from the 2-(3-carboxymethyl-4-halogenophenyl)propionic acid or its salt to give Zaltoprofen (final product) corresponds to Preparation-VI.

1) Preparation of 2-(3-carboxymethyl-4-halogenophenyl) propionic acid or its salt The preparation can be performed in the manner as described in Preparation II.

2) Preparation of 2-[3-carboxymethyl-4-(2-carboxyphenythio)phenyl]propionic acid or its salt The above-mentioned 2-(3-carboxymethyl-4-halogenophenyl)propionic acid or its salt is reacted in a polar solvent (e.g., DMSO, DMF, or water) under basic conditions (for instance, in the presence of potassium hydroxide or potassium carbonate) at 25 to 120° C. in the presence of a catalyst (e.g., potassium iodide, powdery copper, or copper salt).

3) Preparation of 2-[3-(lower)alkoxycarbonylmethyl-4-(2-(lower)alkoxycarbonylphenylthio)phenyl]propionic acid (lower)alkyl ester The preparation can be performed in the manner as described in Preparation III.

4) Preparation of 2-(10,11-dihydro-11-(lower) alkoxycarbonyl-10-oxodibenzo[b,f]thiepin-2-yl)propionic acid (lower)alkyl ester by cyclization of 2-[3-(lower) alkoxycarbonylmethyl-4-(2-(lower) alkoxycarbonylphenylthio)phenyl]propionic acid lower alkyl ester The preparation can be performed in the manner as described in Preparation III.

5) Preparation of Zaltoprofen by hydrolysis and decarboxylation of 2-(10,11-dihydro-11-(lower)alkoxycarbonyl-10-oxodibenzo[b,f]thiepin-2-yl)propionic acid (lower)alkyl ester The process described in the aforementioned Preparation-III can be utilized.

The starting compound employed for the aforementioned various processes for the preparation of Zaltoprofen, that is, 2-(4-amino-3-carboxymethylphenyl)propionic acid or its salt is, as stated hereinbefore, a new compound. This new compound can be produced from a known compound in the manners described below.

(1) Production of 2-(4-amino-3-carboxymethylphenyl) propionic acid or its salt—Production-(1)

2-(3-Halogeno-4-nitrophenyl)-2-methylmalonic acid diester is reacted with an acetic acid ester derivative [which is represented by the formula of $R^1$—$CH_2$—$COOR^2$ (each of $R^1$ and $R^2$ has the meaning defined hereinbefore) and can be exemplified by malonic acid dialkyl ester, acetoacetic acid ester, and cyanoacetic acid ester] to give the methylmalonic acid derivative having the aforementioned formula (A); the methylmalonic acid derivative is subjected to hydrolysis and decarboxylation to give 2-(3-carboxymethyl-4-nitrophenyl)propionic acid or its salt; and finally the resulting compound is reduced to give the desired compound. Production-(1) is illustrated in the following Reaction Scheme V.

[Reaction Scheme V]

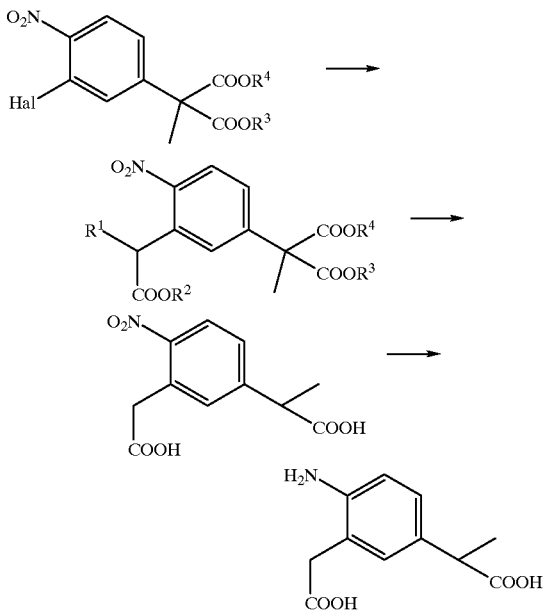

1) Production of the methylmalonic acid derivative having the formula (A)

The desired compound can be produced by reacting 2-(3-halogeno-4-nitrophenyl)-2-methylmalonic acid diester (in which "halogeno" means fluoro, chloro, or bromo) with an acetic acid ester derivative [e.g., malonic acid dialkyl ester having alkyl of 1–6 carbon atoms, such as dimethyl malonate; acetoacetic acid ester such as methyl acetoacetate or ethyl acetoacetate; or cyanoacetic acid ester such as methyl cyanoacetate or ethyl cyanoacetate).

The reaction is preferably carried out in an anhydrous organic solvent such as anhydrous dimethylformamide in the presence of a basic compound such as potassium tert-butoxide or sodium hydride, in an inert gas atmosphere such as a nitrogen gas atmosphere. The reaction temperature generally is in the range of from 50° C. (preferably from 70° C.) to the boiling temperature of the reaction solvent. A representative compound of the 2-(3-halogeno-4-nitrophenyl)-2-methylmalonic acid dialkyl ester employed in the above production process is diethyl 2-(3-chloro-4-nitrophenyl)-2-methylmalonate, which is known and described in Japanese Patent Publication No. 47-45746.

2) Production of 2-(3-carboxymethyl-4-nitrophenyl) propionic acid or its salt

This compound can be produced by subjecting the methylmalonic acid derivative of the formula (A) [which is obtained in the 1) above] to reactions for hydrolysis and decarboxylation. The hydrolysis and decarboxylation can be carried out, for instance, in an aqueous acetic acid solution in the presence of concentrated sulfuric acid as catalyst. The reactions can be performed simultaneously or successively by heating the reaction solution under reflux.

3) Production of 2-(4-amino-3-carboxymethylphenyl) propionic acid or its salt

This compound can be produced by reducing the 2-(3-carboxymethyl-4-nitrophenyl)propionic acid or its salt [which is obtained in the 2) above] under basic conditions (in an aqueous alkaline solution containing, for instance, sodium hydroxide, potassium hydroxide, lithium hydroxide, or sodium carbonate). The salt of 2-(4-amino-3-carboxymethylphenyl)propionic acid can be a disodium salt, a dipotassium salt, or a dilithium salt. The reduction can be performed utilizing hydrogen gas in the presence of palladium/carbon.

(2) Production of 2-(4-amino-3-carboxymethylphenyl) propionic acid or its salt—Production-(2)

2,4-Dihalogenonitrobenzene (known compound) is reacted successively with methylmalonic acid diester (e.g., dialkyl methylmalonate) and the aforementioned acetic acid ester derivative, to give the methylmalonic acid derivative of the formula (A); the methylmalonic acid derivative is then subjected to hydrolysis and decarboxylation, to give 2-(3-carboxymethyl-4-nitrophenyl)propionic acid or its salt; and finally the product is reduced to give the desired compound. Production-(2) is illustrated in the following Reaction Scheme VI.

[Reaction Scheme VI]

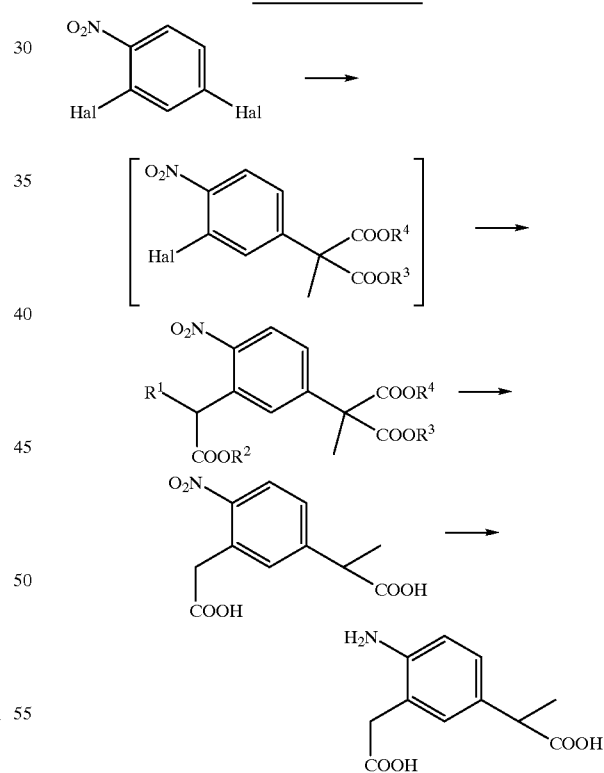

1) Production of the methylmalonic acid derivative having the formula (A)

2,4-Dihalogenonitrobenzene (in which "halogeno" means, for instance, chloro or bromo) is reacted successively with a methylmalonic acid diester (e.g., dialkyl methylmalonate such as diethyl methylmalonate) and the above-mentioned acetic acid ester derivative. The reaction can be carried out by utilizing the procedures described in the aforementioned Production-(1)-1).

2) Production of 2-(3-carboxymethyl-4-nitrophenyl) propionic acid or its ester

The production can be performed in the manner as described in the above-mentioned Production-(1).

3) Production of 2-(4-amino-3-carboxymethylphenyl) propionic acid or its salt

The production can be performed in the manner as described in the above-mentioned Production-(1).

(3) Production of 2-(4-amino-3-carboxymethylphenyl) propionic acid or its salt—Production-(3)

The methylmalonic acid derivative of the formula (A) is first reduced to convert into a methylmalonic acid derivative of the formula (B), and the resulting derivative is then subjected to hydrolysis and decarboxylation. Production-(3) is illustrated in the following Reaction Scheme VII.

[Reaction Scheme VII]

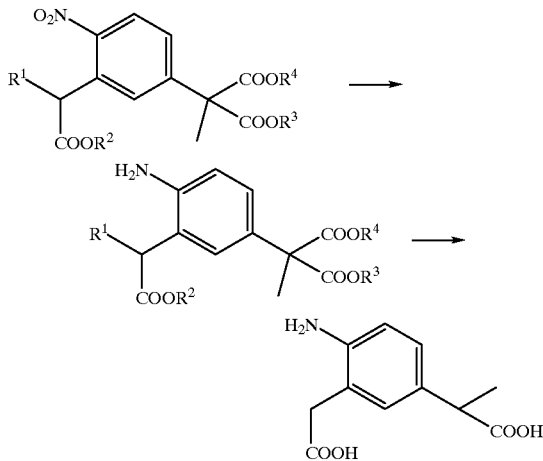

1) Production of the methylmalonic acid derivative of the formula (B) by reduction of the methylmalonic acid derivative of the formula (A)

The reduction can be performed by bringing the methylmalonic acid derivative of the formula (A) into contact with hydrogen gas at −10 to 100° C. in the presence of palladium/carbon.

2) Hydrolysis and decarboxylation of the methylmalonic acid derivative of the formula (B)

The hydrolysis and decarboxylation can be carried out in the same manner as the hydrolysis and decarboxylation of the methylmalonic acid derivative of the formula (A) which is described in the Production-(1).

The present invention is further described by the following examples.

EXAMPLE 1

Preparation (I) of 2-(3-carboxymethyl-4-nitrophenyl)propionic acid (1) Preparation of diethyl 2-3-bis(methoxycarbonyl)methyl-4-nitrophenyl]-2-methylmalonate Dimethyl malonate (4.04 g, 30.6 mmol.), potassium t-butoxide (3.43 g, 30.6 mmol.) and anhydrous N,N-dimethylformamide (15 mL) were mixed and stirred at 90° C. for 10 minutes in a nitrogen atmosphere. The mixture was then cooled to room temperature, and to the cooled mixture was added a solution of diethyl 2-(3-chloro-4-nitrophenyl)-2-methylmalonate (5.04 g, 15.3 mmol., prepared in the manner as described in Japanese Patent Publication No. 47-45,746) in anhydrous N,N-dimethylformamide (15 mL).

The resulting mixture was stirred at 90° C. for 3 hours, and then poured into 1N hydrochloric acid (30 mL). The mixture was subjected to extraction using two portions of diethyl ether. The ether extracts were combined, washed successively with water and an aqueous saturated sodium chloride solution, and dried over anhydrous sodium sulfate. The dried extract was placed under reduced pressure to give 7.97 g of a yellow oil. The oil was adsorbed on silica gel (16 g) and subjected to moderate pressure silica gel column chromatography. The adsorbed oil was eluted using a mixture of ethyl acetate/hexane (1/3, v/v) to give 4.33 g (yield: 66.7%) of the desired compound as a yellow oil.

$^1$H-NMR (CDCl$_3$)δ: 1.27 (6H, t, J=7 Hz), 1.88 (3H, s), 3.80 (6H, s), 4.24 (2H, q, J=7 Hz), 4.25 (2H, q, J=7 Hz), 5.35 (1H, s), 7.55 (1H, dd, J=2 Hz, 8 Hz), 7.57 (1H, d, J=2 Hz), 8.05 (1H, d, J=8 Hz).

(2) Preparation of 2-(3-carboxymethyl-4-nitrophenyl) propionic acid

The diethyl 2-[3-bis(methoxycarbonyl)methyl-4-nitrophenyl]-2-methylmalonate (obtained in (1) above, 4.13 g, 9.71 mmol.) was dissolved in acetic acid (40 mL). To the solution were added water (16 mL) and concentrated sulfuric acid (4 mL), and the resulting mixture was heated for 15 hours under reflux. The acetic acid was distilled off under reduced pressure. The residue was concentrated under reduced pressure after addition of toluene. The precipitated crystals were collected by filtration and washed with water to give 2.06 g of the desired compound as a pale brown crystalline product. The filtrate and washing were combined and subjected to extraction using ethyl acetate. The ethyl acetate portion was washed successively with water and an aqueous saturated sodium chloride solution, and dried over anhydrous sodium sulfate. The solvent was distilled off under reduced pressure to leave 0.32 g of the desired compound as a yellow crystalline product. The total amount was 2.38 g (yield: 96.8%).

m.p.: 169–171° C. (after recrystallization from ethyl acetate and hexane); $^1$H-NMR (CD$_3$OD)δ: 1.51 (3H, d, J=7 Hz), 3.86 (1H, q, J=7 Hz), 4.04 (2H, s), 7.42 (1H, d, J=2 Hz), 7.49 (1H, dd, J=2 Hz, 8 Hz), 8.09 (1H, d, J=8 Hz). IR ?$_{max}$ (KBr) cm$^{-1}$: 2980, 1700, 1610, 1585, 1515, 1450, 1430, 1340, 1300, 1250, 1230, 930.

EXAMPLE 2

Preparation (II) of 2-(3-carboxymethyl-4-nitrophenyl)propionic acid

In anhydrous N,N-dimethylformamide (20 mL) were dissolved 2,4-dichloronitrobenzene (3.84 g, 20 mmol.) and diethyl methylmalonate (5.23 g, 30 mmol.). To this was added potassium t-butoxide (3.37 g, 30 mmol.) with stirring under chilling with ice. The resulting mixture was further stirred for 5 minutes under chilling with ice, and then for 18 hours at room temperature.

Independently, dimethyl malonate (5.28 g, 40 mmol.), potassium t-butoxide (4.48 g, 40 mmol.), and anhydrous N,N-dimethylformamide (20 mL) were mixed, and then stirred at 90° C. for 10 minutes. The reaction mixture was cooled to room temperature, and stirred at 90° C. for 4 hours after addition of the aforementioned reaction mixture. The resulting reaction mixture was poured into a mixture of 2N hydrochloric acid (40 mL) and ice, and extracted with two portions of diethyl ether. The diethyl ether portions were combined, washed successively with water and an aqueous saturated sodium chloride solution, and dried over anhydrous sodium sulfate. The dried solution was placed under reduced pressure to distill off the solvent, to leave 7.70 g of a dark brown oil.

Thus obtained crude diethyl 2-[3-bis(methoxycarbonyl) methyl-4-nitrophenyl]-2-methylmalonate was dissolved in acetic acid (80 mL), and heated under reflux for 14 hours, after addition of water (32 mL) and concentrated sulfuric acid (8 mL). The acetic acid was then distilled off under reduced pressure to leave a residue. The residue was diluted with water, and extracted with ethyl acetate. The ethyl acetate portion was washed successively with water and an aqueous saturated sodium chloride solution, and dried over anhydrous sodium sulfate. The solvent was distilled off under reduced pressure to leave 3.50 g of a dark brown crystalline product. The crystalline product was washed with chloroform to give 2.27 g (yield: 44.8%) of the desired compound as a brown crystalline product.

EXAMPLE 3

Preparation (III) of 2-(3-carboxymethyl-4-nitrophenyl)propionic acid (1) Preparation of diethyl 2-[3-[acetyl(methoxycarbonyl) methyl]-4-nitrophenyl]-2-methylmalonate To a solution of diethyl 2-(3-chloro-4-nitrophenyl)-2-methylmalonate (1.0 g, 3.03 mmol.) in dimethyl sulfoxide (DMSO, 3mL) were added potassium carbonate (1.25 g, 9.09 mmol.) and methyl acetoacetate (0.99 mL, 9.0 mmol.). The resulting mixture was stirred at 70° C. for 6 hours. The reaction mixture was cooled to room temperature, neutralized with diluted hydrochloric acid, and extracted with ethyl acetate. The ethyl acetate portion was washed with an aqueous saturated sodium chloride solution, and dried over magnesium sulfate. The dried portion was concentrated to leave a residue. The residue was purified by silica gel column chromatography (Wako Gel C-330, available from Wako Jyunyaku Industry Co., Ltd., toluene/ethyl acetate= 100/4, v/v), to give 0.64 g (yield: 52%) of the desired compound as a yellow oil.

$^1$H-NMR (CDCl$_3$)δ: 1.15–1.35 (6H, m), 1.87 (3H, s), 1.89 (3H, s), 3.63 (3H, s), 4.18–4.30 (4H, m), 7.32 (1H, s), 7.48 (1H, d, J=9 Hz), 7.99 (1H, d, J=9 Hz), 12.92 (1H, s). CI-MASS(m/e): 410(M+1), 378, 336

(2) Preparation of 2-(3-carboxymethyl-4-nitrophenyl) propionic acid

In methanol (1 mL) was dissolved diethyl 2-[3-[acetyl (methoxycarbonyl)methyl]-4-nitrophenyl]-2-methylmalonate (obtained in (1) above, 50.9 mg, 0.124 mmol.). The resulting solution was stirred for 15 hours at room temperature after addition of 2M aqueous sodium hydroxide solution (1.5 mL, 3 mmol.). The reaction mixture was then stirred at 60° C. for 3 hours after addition of 6M hydrochloric acid (1 mL, 3 mmol.). The mixture was cooled and extracted with ethyl acetate. The ethyl acetate portion was washed with an aqueous saturated sodium chloride solution and dried over anhydrous magnesium sulfate. The dried organic portion was concentrated and purified by silica gel column chromatography (Wako Gel C-200, available from Wako Jyunyaku Industry Co., Ltd., hexane/ethyl acetate/acetic acid=7/3/1, v/v/v), to give 20.3 mg (yield: 65%) of the desired compound.

EXAMPLE 4

Preparation (IV) of 2-(3-carboxymethyl-4-nitrophenyl)propionic acid (1) Preparation of diethyl 2-[3-[cyano(ethoxycarbonyl) methyl]-4-nitrophenyl]-2-methylmalonate Diethyl 2-(3-chloro-4-nitrophenyl)-2-methylmalonate (119 mg, 0.36 mmol.), ethyl cyanoacetate (81 mg, 0.72 mmol.), powdery potassium carbonate (119 mg, 0.86 mmol.), and dimethyl sulfoxide (1 mL) were mixed and stirred at 80° C. for 2 hours. The reaction mixture was cooled to room temperature, and washed with diethyl ether after addition of water. The aqueous portion was made acidic by addition of 6N hydrochloric acid, and extracted with diethyl ether. The ether portion was washed successively with water and an aqueous saturated sodium chloride solution, and dried over anhydrous sodium sulfate. The solvent was distilled off to give 133 mg (yield: 92%) of the desired compound as a yellow oil.

$^1$H-NMR (CDCl$_3$)δ: 1.28 (3H, t, J=7 Hz), 1.28 (3H, t, J=7 Hz), 1.33 (3H, t, J=7 Hz), 1.92 (3H, s), 4.2–4.4 (6H, m), 5.69 (1H, s), 7.66 (1H, dd, J=2 Hz, 9 Hz), 7.82 (1H, d, J=2 Hz), 8.20 (1H, d, J=9 Hz).

(2) Preparation of 2-[3-cyano(ethoxycarbonyl)methyl-4-nitrophenyl]-2-propionic acid In dimethyl sulfoxide (1.5 mL) was dissolved diethyl 2-[3-[cyano(ethoxycarbonyl)methyl]-4-nitrophenyl]-2-methylmalonate (obtained in the same manner as that of the above (1), 163 mg, 0.4 mmol.). The solution was stirred for 40 hours at room temperature after addition of 4N aqueous sodium hydroxide solution (1.5 mL). The reaction mixture was made acidic by addition of 2N hydrochloric acid, and extracted with toluene. The toluene portion was washed successively with water and an aqueous saturated sodium chloride solution, and dried over sodium sulfate. The solvent was distilled off under reduced pressure to give 112 mg (yield: 92%) of the desired compound as a yellow oil.

$^1$H-NMR (CDCl$_3$)δ: 1.33 (3H, t, J=7 Hz), 1.60 (3H, d, J=7 Hz), 3.91 (1H, q, J=7 Hz), 4.31 (2H, q, J=7 Hz), 5.65, 5.66 (1H, s×2), 7.60 (1H, dd, J=1Hz, 8 Hz), 7.69 (1H, d, J=1Hz), 8.21 (1H, d, J=8 Hz).

(3) Preparation of 2-(3-cyanomethyl-4-nitrophenyl)-2-propionic acid

In acetic acid (0.4 mL) was dissolved 2-[3-cyano (ethoxycarbonyl)methyl-4-nitrophenyl]-2-propionic acid (obtained in (2) above, 110 mg, 0.36 mmol.). The solution was heated for 4 hours under reflux, after addition of water (0.36 mL) and concentrated sulfuric acid (0.04 mL). The reaction mixture was diluted with water and extracted with ethyl acetate. The ethyl acetate portion was washed successively with water and an aqueous saturated sodium chloride solution, and dried over anhydrous sodium sulfate. The solvent was distilled off under reduced pressure to leave a dark red oil. The oil was adsorbed on silica gel and subjected to silica gel column chromatography. The elution was performed using a mixture of acetic acid and chloroform (1/100, v/v), to give 61 mg (yield: 72%) of the desired compound as a white crystalline product.

m.p.: 55–59° C.;

$^1$H-NMR (CDCl$_3$)δ: 1.60 (3H, d, J=7 Hz), 3.90 (1H, q, J=7 Hz), 4.21 (2H, s), 7.52 (1H, dd, J=2 Hz, 9 Hz), 7.65 (1H, d, J=2 Hz), 8.18 ($_1$H, d, J=9 Hz). IR ν$_{max}$ (KBr) cm$^{-1}$: 3000, 2260, 1720, 1615, 1590, 1530, 1420, 1340.

(4) Preparation of 2-(3-carboxymethyl-4-nitrophenyl) propionic acid

In acetic acid (0.3 mL) was dissolved 2-(3-cyanomethyl-4-nitrophenyl)-2-propionic acid (obtained in (3) above, 14 mg, 0.06 mmol.). The solution was heated for 24 hours under reflux, after addition of water (0.27 mL) and concentrated sulfuric acid (0.03 mL). The reaction mixture was diluted with water and extracted with ethyl acetate. The ethyl acetate portion was washed successively with water and an aqueous saturated sodium chloride solution, and dried over anhydrous sodium sulfate. The solvent was distilled off under reduced pressure to leave a residue. The residue was dissolved in toluene and concentrated under reduced pressure to give 13 mg (yield: 85%) of the desired compound as a brown crystalline product.

m.p.: 169–171° C. (after recrystallization from ethyl acetate and hexane).

EXAMPLE 5

Preparation (V) of 2-(3-carboxymethyl-4-nitrophenyl)propionic acid

In anhydrous dimethyl sulfoxide (10 mL) was suspended 60% sodium hydride (1.04 g, 26 mmol.). To the suspension was dropwise added diethyl methylmalonate (5.0 mL, 29 mmol.) for 2 minutes, while the suspension was stirred under cooling with water. The mixture was stirred at 60–100° C. for 30 minutes. To the resulting homogeneous solution was dropwise added a solution of 2,4-dichloronitrobenzene (3.84 g, 20 mmol.) in anhydrous dimethyl sulfoxide (4 mL) for 5 minutes, while the solution was stirred under cooling with water. The resulting mixture was then stirred at 50° C. for 2 hours. The reaction mixture was stirred at 70° C. for 2 hours, after addition of ethyl cyanoacetate (5.3 mL, 50 mmol.) and powdery potassium carbonate (13.8 g, 100 mmol.). To the resulting reaction mixture was added 3N hydrochloric acid, while the mixture was stirred under cooling with water. The mixture was extracted with toluene. The toluene portion was washed successively with an aqueous 200 potassium carbonate solution (14 mL), water, 2N hydrochloric acid (5 mL), water and an aqueous saturated sodium chloride solution, and then dried over anhydrous sodium sulfate. The solvent was distilled off under reduced pressure to leave an orange oil (12.0 g). The obtained orange oil was placed under reduced pressure to distill the solvent off, to give 8.5 g of a crude diethyl 2-[3-[cyano(ethoxycarbonyl)methyl]-4-nitrophenyl]-2-methylmalonate as an orange oil. The crude product was dissolved in acetic acid (30 mL), and heated for 60 hours under reflux after addition of water (24 mL) and concentrated sulfuric acid (6 mL). The upper colorless oil layer was separated and removed. The acetic acid was distilled off under reduced pressure. The residue was dissolved in toluene and concentrated under reduced pressure. This concentration procedure was repeated once, and to the residue were added water (20 mL) and chloroform (10 mL). Insolubles were filtered off, and to the filtrate was added a small amount of separately obtained crystals of 2-(3-carboxymethyl-4-nitrophenyl)propionic acid. The precipitated crystals were collected by filtration and washed successively with three portions of water, chloroform, and hexane. The washed crystalline product was air-dried, and then dried under reduced pressure, to give 2.20 g (yield: 43%) of the desired compound as a pale brown powder.

EXAMPLE 6

Preparation (VI) of 2-(3-carboxymethyl-4-nitrophenyl)propionic acid

In acetic acid (1 mL) was dissolved diethyl 2-[3-[cyano (ethoxycarbonyl)methyl]-4-nitrophenyl]-2-methylmalonate (obtained in the same manner as in Example 5, 406 mg, 1 mmol.). The solution was heated for 36 hours under reflux, after addition of water (0.9 mL) and concentrated sulfuric acid (0.1 mL). The reaction mixture was diluted with water, and then extracted with ethyl acetate. The ethyl acetate portion was washed successively with water and an aqueous saturated sodium chloride solution, and dried over anhydrous sodium sulfate. The solvent was distilled off under reduced pressure, to give 189 mg (yield: 75%) of the desired compound as a brown crystalline product.

EXAMPLE 7

Preparation (I) of 2-(4-amino-3-carboxymethylphenyl)propionic acid disodium salt In 0.5N aqueous sodium hydroxide solution (0.8 mL) was dissolved 2-(3-carboxymethyl-4-nitrophenyl)propionic acid (obtained in Example 1, 50 mg, 0.2 mmol.). The solution was stirred for 18 hours at room temperature in a hydrogen gas atmosphere, after addition of 10% palladium/carbon (10 mg). Insolubles were removed by filtration, and the filtrate was concentrated under reduced pressure to give 55 mg (yield: quantitative amount) of the desired compound as a colorless oil.

$^1$H-NMR (D$_2$O)δ: 1.37 (3H, d, J=7 Hz), 3.45 (2H, s), 3.54 (1H, q, J=7 Hz), 6.83 (1H, d, J=8 Hz), 7.0–7.1 (2H, m).

EXAMPLE 8

Preparation (II) of 2-(4-amino-3-carboxymethylphenyl)propionic acid disodium salt In 1N aqueous sodium hydroxide solution (6 mL) was dissolved 2-(3-carboxymethyl-4-nitrophenyl)propionic acid (obtained in Example 1, 760 mg, 3 mmol.). The solution was stirred for 18 hours at room temperature in a hydrogen gas atmosphere, after addition of 1006 palladium/carbon (15 mg). Insolubles were removed by filtration, and the filtrate was concentrated under reduced pressure to give a brown crystalline product. The obtained crystalline product was washed successively with ethanol and hexane to give 734 mg (yield: 91.7%) of the desired compound as a white crystalline product.

m.p.: 160–163° C.

$^1$H-NMR (D$_2$O)δ: 1.37 (3H, d, J=7 Hz), 3.45 (2H, s), 3.54 (1H, q, J=7 Hz), 6.83 (1H, d, J=8 Hz), 7.0–7.1 (2H, m). IR ν$_{max}^\circ$ (KBr) cm$^{-1}$: 3400, 1560, 1400.

EXAMPLE 9

Preparation of diethyl 2-[4-amino-3-bis (methoxycarbonyl)methylphenyl]-2-methylmalonate In ethanol (1 mL) was dissolved diethyl 2-[3-bis-(methoxycarbonyl)methyl-4-nitrophenyl]propionate (obtained in Example 1-(1), 30 mg, 0.07 mmol.). The solution was stirred for 3.5 hours at room temperature in a hydrogen gas atmosphere, after addition of 10% palladium/ carbon (2.5 mg). Insolubles were removed by filtration, and the filtrate was concentrated under reduced pressure to give 28 mg (yield: quantitative amount) of the desired compound as a white crystalline product.

m.p.: 91–92° C. (after recrystallization from ethyl acetate and hexane); $^1$H-NMR (CDCl$_3$)δ: 1.24 (6H, t, J=7 Hz), 1.82 (3H, s), 3.75 (6H, s), 4.21 (4H, q, J=7 Hz), 4.63 (1H, s), 6.68 (1H, d, J=8 Hz), 7.1–7.2 (2H, m).

EXAMPLE 10

Preparation (I) of 2-(3-carboxymethyl-4-phenylthiophenyl)propionic acid

In 2N hydrochloric acid (0.5 mL) was dissolved 2-(4-amino-3-carboxymethylphenyl)propionic acid disodium salt (prepared in Example 7, 53 mg, 0.2 mmol.). Sodium nitrite (14 mg, 0.2 mmol.) was added to the resulting solution under stirring and chilling with ice. The mixture was stirred for 30 minutes under chilling with ice. The mixture was then neutralized with a chilled aqueous saturated sodium acetate solution. To the neutralized mixture was added a solution of thiophenol (0.02 mL, 0.2 mmol.) in 6N aqueous sodium hydroxide solution (0.1 mL), and the mixture was stirred for 2 hours at room temperature. The reaction mixture was then made acidic by addition of 2N hydrochloric acid, and extracted with ethyl acetate. The ethyl acetate portion was extracted with an aqueous saturated sodium hydrogen carbonate solution. The aqueous portion was then made acidic by addition of 6N hydrochloric acid and extracted with ethyl acetate. The ethyl acetate portion was washed successively with water and an aqueous saturated sodium chloride solution, and dried over anhydrous sodium sulfate. The solvent was distilled off under reduced pressure to give 28 mg (yield: 45%) of the desired compound.

EXAMPLE 11

Preparation (II) of 2-(3-carboxymethyl-4-phenylthiophenyl)propionic acid

In 0.5N aqueous sodium hydroxide solution (8 mL) was dissolved 2-(3-carboxymethyl-4-nitrophenyl)propionic acid (prepared in Example 2, 504 mg, 1.99 mmol.). The solution was stirred for 19 hours at room temperature in a hydrogen gas atmosphere after addition of 10% palladium/carbon (50 mg). Insolubles were filtered off and washed with water (8 mL). The filtrate and washing were combined and stirred under chilling with ice. The stirred liquid was made acidic by addition of concentrated hydrochloric acid (1 mL). To this was added sodium nitrite (138 mg, 2 mmol.). The resulting mixture was then stirred at 4–5° C. for 30 minutes. The mixture was neutralized with a chilled aqueous saturated sodium acetate solution, and stirred for 1 hour at room temperature and at 95° C. for 1 hour after addition of a solution of thiophenol (0.25 mL, 2.4 mmol.) in 4N aqueous sodium hydroxide solution (2 mL). The reaction mixture was made acidic by addition of concentrated hydrochloric acid and extracted with ethyl acetate. The ethyl acetate portion was washed with water and extracted with an aqueous saturated sodium hydrogen carbonate solution. The aqueous portion was made acidic by addition of hydrochloric acid and extracted with ethyl acetate. The ethyl acetate portion was washed successively with water and an aqueous saturated sodium chloride solution, and dried over anhydrous sodium sulfate. The solvent was distilled off under reduced pressure, to leave 471 mg of a red oil. The oil was subjected to moderate pressure silica gel column chromatography and eluted with methanol/chloroform (1/40, v/v) mixture, to give 265 mg (yield: 42.1%) of the desired compound as a white crystalline product. m.p. 143–145° C.

EXAMPLE 12

Preparation (I) of 2-(3-carboxymethyl-4-iodophenyl)propionic acid

An aqueous solution (16.05 g) of 2-(4-amino-3-carboxymethylphenyl)propionic acid disodium salt (802 mg, 3.00 mmol.) and sodium hydroxide (107 mg, 2.68 mmol.) was cooled to 4° C., and stirred at 3–5° C. for 4 minutes after addition of 6M(12N) sulfuric acid (1.5 mL) and sodium nitrite (0.23 g, 3.3 mol.). The resulting reaction mixture was stirred at 4° C. for 20 minutes and then at 25° C. for 16 hours, after addition of potassium iodide (1.49 g, 9.0 mmol.). These reactions were performed in an argon gas atmosphere.

The reaction mixture was extracted with ethyl acetate, and the ethyl acetate portion was dried over magnesium sulfate. The dried ethyl acetate portion was analyzed by HPLC (high performance liquid chromatography) to confirm that 196 mg (0.59 mmol., yield: 20%) of 2-(3-carboxymethyl-4-iodophenyl)propionic acid was contained. The ethyl acetate portion was concentrated and subjected to silica gel column chromatography (Wako gel C-200, Walzo Jyunyaku Industry Co., Ltd., hexane/ethyl acetate/acetic acid=7/3/1, v/v/v) to obtain the desired compound as a crystalline product.

$^1$H-NMR (CD$_3$OD)δ: 1.44 (3H, d, J=7 Hz), 3.68 (1H, q, J=7 Hz), 3.78 (2H, s), 6.97 (1H, dd, J=2 Hz, 8 Hz), 7.30 (1H, d, J=2 Hz), 7.79 (1H, d, J=SHz). EI-MASS(m/e): 334(M), 289, 207.

EXAMPLE 13

Preparation (II) of 2-(3-carboxymethyl-4-iodophenyl)propionic acid

The procedures of Example 12 were repeated except for employing copper (I) iodide (99 wt. %, 1.73 g, 9.0 mmol.) in place of potassium iodide, to give an ethyl acetate portion containing 151 mg (0.45 mmol., yield: 15%) of the desired compound. Thereafter, the ethyl acetate portion was processed in the manner as described in Example 12 to give the desired compound as a purified product.

EXAMPLE 14

Preparation of 2-4-bromo-3-(carboxymethyl)phenyl) propionic acid

An aqueous solution (23.65 g) of 2-(4-amino-3-carboxymethylphenyl)propionic acid disodium salt (1.07 g, 4.00 mmol.) and sodium hydroxide (142 mg, 3.55 mmol.) was cooled to 3° C., and stirred at 3–5° C. for 5 minutes after addition of hydrobromic acid (47%, 4.0 mL, 34 mmol.) and sodium nitrite (0.29 g, 4.1 mmol.). The resulting reaction mixture was dropwise added to a mixture of copper(I) bromide (99 wt. %, 0.87 g, 6.0 mmol.) and hydrobromic acid (47%, 2.5 mL, 22 mmol.), for a period of 7 minutes under chilling with ice. The resulting mixture was stirred at 3° C. for 1 hour and then at 25° C. for 1 hour. These reactions were performed in an argon gas atmosphere.

The reaction mixture was extracted with ethyl acetate, and the ethyl acetate portion was dried over magnesium sulfate. The dried ethyl acetate portion was analyzed by HPLC (high performance liquid chromatography) to confirm that 1.02 g (3.56 mmol., yield: 89%) of 2-[4-bromo-3-(carboxymethyl)phenyl]propionic acid was contained. The ethyl acetate portion was concentrated and subjected to silica gel column chromatography (Wako gel C-200, Wako Jyunyaku Industry Co., Ltd., hexane/ethyl acetate/acetic acid=7/3/1, v/v/v) to obtain the desired compound as a purified crystalline product.

$^1$H-NMR (CD$_3$OD)δ: 1.45 (3H, d, J=7 Hz), 3.70 (1H, q, J=7 Hz), 3.78 (2H, s), 7.15 (1H, dd, J=2 Hz, 8 Hz), 7.31 (1H, d, J=2 Hz), 7.53 (1H, d, J=8 Hz). EI-MASS(m/e): 288(M+ 2), 286, 207.

EXAMPLE 15

Preparation of 2-(3-carboxymethyl-4-chlorophenyl) propionic acid

An aqueous solution (23.65 g) of 2-(4-amino-3-carboxymethylphenyl)propionic acid disodium salt (1.07 g, 4.00 mmol.) and sodium hydroxide (142 mg, 3.55 mmol.) was cooled to 3° C., and stirred at 3–5° C. for 5 minutes after addition of hydrochloric acid (36%, 3.9 mL, 47 mmol.) and sodium nitrite (0.29 g, 4.1 mmol.). The resulting mixture was stirred at 3° C. for 20 minutes and then at 25° C. for 1 hour, after addition of copper(I) chloride (95 wt. %, 1.25 g, 12 mmol.). These reactions were performed in an argon gas atmosphere.

The reaction mixture was extracted with ethyl acetate, and the ethyl acetate portion was dried over magnesium sulfate. The dried ethyl acetate portion was concentrated to leave a residue. The residue was subjected to silica gel column chromatography (Wako Gel C-200, Wako Jyunyaku Industry Co., Ltd., hexane/ethyl acetate/acetic acid=7/3/1, v/v/v) to obtain 0.71 g (2.9 mol., yield: 73%) of the desired compound as a crystalline product.

$^1$H-NMR (CD$_3$OD)δ: 1.45 (3H, d, J=7 Hz), 3.71 (1H, q, J=7 Hz), 3.75 (2H, s), 7.1–7.4 (3H, m). EI-MASS(m/e): 242(M), 197, 163.

EXAMPLE 16

Preparation (III) of 2-(3-carboxymethyl-4-phenylthiophenyl)propionic acid 0.3 M Aqueous potassium hydroxide solution (10 mL, oxygen was removed by addition of 20 mg of sodium hydrosulfite in advance) was mixed with 2-(3-carboxymethyl-4-iodophenyl)propionic acid (prepared in the manner as described in Example 12, 203 mg, 0.607 mmol.) and thiophenol (95 wt. %, 94 mg, 0.81 mmol.). The resulting mixture was heated for 19 hours under reflux (temperature: approx. 100° C.) after addition of 20 mg of powdery copper. The reaction mixture was cooled, made acidic by addition of hydrochloric acid, and extracted with ethyl acetate. The ethyl acetate portion was extracted with an aqueous saturated sodium hydrogen carbonate solution. The aqueous portion was washed with ethyl acetate, made acidic by addition of hydrochloric acid, and extracted with ethyl acetate. The ethyl acetate portion was washed with an aqueous sodium chloride solution, dried over magnesium sulfate, and concentrated to leave a residue. The residue was subjected to silica gel column chromatography (Wako Gel C-200, Wako Jyunyaku Industry Co., Ltd., hexane/ethyl acetate/acetic acid=7/3/1, v/v/v) to obtain 133 mg (0.420 mmol., yield: 69%) of the desired compound.

EXAMPLE 17

Preparation (IV) of 2-(3-carboxymethyl-4-phenylthiophenyl)propionic acid 2-(3-Carboxymethyl-4-iodophenyl)propionic acid (prepared in the manner as described in Example 12, 202 mg, 0.605 mol.), potassium carbonate (380 mg, 2.8 mmol.), N,N-dimethylformamide (DMF, 10 mL), and thiophenol (95 wt. %, 92 mg, 0.79 mmol.) were mixed. The resulting mixture was heated for 19 hours under reflux (temperature: approx. 115° C.) after addition of 20 mg of powdery copper. The reaction mixture was cooled, made acidic by addition of hydrochloric acid, and extracted with ethyl acetate. The ethyl acetate portion was washed with an aqueous sodium chloride solution, dried over magnesium sulfate, and concentrated to leave a residue. The residue was subjected to silica gel column chromatography (Wako gel C-200, Wako Jyunyaku Industry Co., Ltd., hexane/ethyl acetate/acetic acid=7/3/1, v/v/v) to obtain 94 mg (0.30 mmol., yield: 49%) of the desired compound.

EXAMPLE 18

Preparation of 2-(10,11-dihydro-10-oxodibenzo[b,f]thiepin-2-yl)propionic acid [i.e., Zaltoprofen]

2-(3-Carboxymethyl-4-phenylthiophenyl)propionic acid (prepared in the manner as described in Example 10, 174 mg, 0.55 mmol.) was mixed with polyphosphoric acid (3.5 g). The mixture was stirred at 60–70° C. for 3 hours. The reaction mixture was then extracted with ethyl acetate after addition of chilled water. The ethyl acetate portion was washed successively with water and an aqueous saturated sodium chloride solution, and dried over anhydrous sodium sulfate. The solvent was distilled off under reduced pressure to leave a brown crystalline residue. The residue was recrystallized from benzene-hexane, to give 123 mg (yield: 75%) of the desired compound as a pale yellow crystalline product. m.p. 130.5–131.5° C.

$^1$H-NMR (CDCl$_3$)δ: 1.49 (3H, d, J=7 Hz), 3.73 (1H, q, J=7 Hz), 4.36 (2H, s), 7.16 (1H, dd, J=2 Hz, 8 Hz), 7.3–7.5 (3H, m), 7.5–7.6 (2H, m), 8.19 (1H, dd, J=1Hz, 8 Hz).

EXAMPLE 19

Preparation (I) of 2-[3-carboxymethyl-4-(2-carboxyphenylthio)phenyl]propionic acid In 1N aqueous sodium hydroxide solution (12 mL) was dissolved 2-(3-carboxymethyl-4-nitrophenyl)propionic acid (prepared in Example 2, 1.52 g, 6.0 mmol.). The resulting solution was stirred for 41 hours at room temperature in a hydrogen gas atmosphere, after addition of 10% palladium/carbon (0.03 g). Insolubles were filtered off and washed with water. The filtrate and washing were combined. This was stirred under chilling with ice and made acidic by addition of concentrated hydrochloric acid (2.5 mL). The acidic solution was stirred at 50C for 30 minutes after addition of sodium nitrite (0.42 g, 6.1 mmol.). To the resulting aqueous diazonium salt solution was dropwise added a solution of thiosalicylic acid (1.39 g, 9.0 mmol.) in 4N aqueous sodium hydroxide solution (12 mL) at 5–15° C. for a period of 2 minutes. After the dropwise addition was complete, the mixture was stirred at room temperature for 1 hour and at 95° C. for 1 hour. The reaction mixture was made acidic by addition of concentrated hydrochloric acid and extracted with three portions of ethyl acetate. The ethyl acetate portions were combined, washed successively with water and an aqueous saturated sodium chloride solution, and finally dried over anhydrous sodium sulfate. The solvent was distilled off under reduced pressure to leave 2.98 g of a brown solid residue. The residue was suspended in ethyl acetate, and insolubles were filtered off. The filtrate was concentrated under reduced pressure after addition of silica gel (4.2 g). The concentrate was subjected to moderate pressure silica gel column chromatography and eluted with acetic acid/chloroform (1/10, v/v), to give 0.30 g of the desired compound as a yellow crystalline product.

m.p.: 229–232° C. $^1$H-NMR (CD$_3$OD)δ: 1.51 (3H, d, J=7 Hz), 3.76 (2H, s), 3.79 (1H, q, J=7 Hz), 6.67 (1H, dd, J=1Hz, 8 Hz), 7.14 (1H, ddd, J=1Hz, 7 Hz, 8 Hz), 7.24, (1H, ddd, J=2 Hz, 7 Hz, 8 Hz), 7.34 (1H, dd, J=2 Hz, 8 Hz), 7.44 (1H, d, J=2 Hz), 7.52 (1H, d, J=8 Hz), 7.99 (1H, dd, J=2 Hz, 8 Hz). IR $v_{max}$ (KBr) cm$^{-1}$: 2980, 1700, 1465, 1410, 1310, 1255, 1230, 750.

EXAMPLE 20

Preparation (II) of 2-[3-carboxymethyl-4-(2-carboxyphenylthio)phenyl]propionic acid In 2N hydrochloric acid (1.5 mL) was dissolved 2-(4-amino-3-carboxymethylphenyl)propionic acid disodium salt (prepared in the manner as described in Example 8, 134 mg, 0.5 mmol.). To the resulting solution was added sodium nitrite (35 mg, 0.5 mmol.) under stirring and chilling with ice. The mixture was stirred at 50C for 30 minutes. To the resulting aqueous diazonium salt solution was dropwise added a solution of thiosalicylic acid (154 mg, 1.0 mmol.) in 4N aqueous sodium hydroxide solution (2 mL). After the dropwise addition was complete, the mixture was stirred at room temperature for 1 hour and at 95° C. for 1 hour. The reaction mixture was made acidic by addition of 2N hydrochloric acid and extracted with ethyl acetate. The ethyl acetate portion was washed successively with water and an aqueous saturated sodium chloride solution, and finally dried over anhydrous sodium sulfate. The solvent was distilled off under reduced pressure to leave 230 mg of a brown solid residue. The residue was suspended in ethyl acetate, and insolubles were filtered off. The filtrate was concentrated under reduced pressure after addition of silica gel (0.4 g). The concentrate was subjected to moderate pressure silica gel column chromatography and eluted with acetic acid/chloroform (1/10, v/v), to give 24 mg of the desired compound as a white crystalline product.

EXAMPLE 21

Preparation of methyl 2-[3-methoxycarbonylmethyl-4-(2-methoxycarbonylphenylthio)phenyl]propionate 2-[3-Carboxymethyl-4-(2-carboxyphenylthio)phenyl]propionic acid (72 mg, 0.2 mmol.), methanol (0.8 mL), trimethyl orthoformate (0.2 mL), and concentrated sulfuric acid (0.05 mL) were mixed, and the mixture was heated for 6 hours under reflux. The reaction mixture was diluted with water and washed with diethyl ether. The diethyl ether portion was washed successively with water and an aqueous saturated sodium chloride solution, and dried over anhydrous sodium sulfate. The solvent was distilled off under reduced pressure to give 78 mg of the desired compound as a colorless oil.

$^1$H-NMR (CDCl$_3$)δ: 1.55 (3H, d, J=7 Hz), 3.54 (3H, s), 3.71 (3H, s), 3.78 (1H, q, J=7 Hz), 3.81 (2H, s), 3.95 (3H, s), 6.65 (1H, d, J=8 Hz), 7.11 (1H, dd, J=7 Hz, 8 Hz), 7.22 (1H, dd, J=7 Hz, 8 Hz), 7.29 (1H, dd, J=2 Hz, 8 Hz), 7.36 (1H, d, J=2 Hz), 7.55 (1H, d, J=8 Hz), 7.98 (1H, d, J=8 Hz).

EXAMPLE 22

Preparation of methyl 2-(10,11-dihydro-11-methoxycarbonyl-10-oxodibenzo[b,f]thiepin-2-yl)propionate Methyl 2-[3-methoxycarbonylmethyl-4-(2-methoxycarbonylphenylthio)phenyl]propionate (prepared in Example 21, 78 mg, 0.19 mmol.), toluene (1 mL) and potassium t-butoxide (43 mg, 0.38 mmol.) were mixed, and the mixture was stirred for 16 hours at room temperature. The reaction mixture was then extracted with ethyl acetate after addition of 2N hydrochloric acid. The ethyl acetate portion was washed with an aqueous saturated sodium chloride solution, and dried over anhydrous sodium sulfate. The dried ethyl acetate portion was placed under reduced pressure to distill the solvent off, to leave 78 mg of a pale yellow oil. The oil was subjected to moderate pressure silica gel column chromatography and eluted with ethyl acetate/hexane (1/4, v/v), to give 21 mg of the desired compound as a colorless oil (a mixture of 1:1 diastereomers). The following NMR data are those of the 1:1 diastereomers.

$^1$H-NMR (CDCl$_3$)δ: 1.44 (3H, d, J=7 Hz), 1.44 (3H, d, J=7 Hz), 3.63 (3H, s), 3.63 (3H, s), 3.66 (1Hx2, q, J=7 Hz), 3.84 (3H, s), 3.85 (3H, s), 7.1–7.4 (8H, m), 7.4–7.6 (4H, m), 7.7–7.8 (2H, m), 13.77 (1H, s), 13.77 (1H, s).

EXAMPLE 23

Preparation of 2-(10,11-dihydro-11-oxodibenzo[b,f]thiepin-2-yl)propionic acid

Methyl 2-(10,11-dihydro-1i-methoxycarbonyl-10-oxodibenzo[b,f]thiepin-2-yl)propionate (prepared in Example 22, 18 mg, 0.040 mmol.), acetic acid (0.3 mL) and 6N hydrochloric acid (0.3 mL) were mixed, and the mixture was heated for 2 hours under reflux. To the reaction mixture was added water, and the aqueous mixture was extracted with ethyl acetate. The ethyl acetate portion was washed successively with water and an aqueous saturated sodium chloride solution, and dried over anhydrous sodium sulfate. The dried ethyl acetate portion was placed under reduced pressure to distill the solvent off. The residue was dissolved in toluene and concentrated under reduced pressure to give 14 mg of the desired compound as a white crystalline product.

m.p.: 130.5–131.5° C.; $^1$H-NKR (CDCl$_3$)δ: 1.49 (3H, d, J=7 Hz), 3.73 (1H, q, J=7 Hz), 4.36 (2H, s), 7.16 (1H, dd, J=2 Hz, 8 Hz), 7.3–7.5 (3H, m), 7.5–7.6 (2H, m), 8.19 (1H, dd, J=1Hz, 8 Hz).

EXAMPLE 24

Preparation (III) 2-[3-carboxymethyl-4-(2-carboxyphenylthio)phenyl]propionic acid 0.2 M Aqueous potassium hydroxide solution (5 mL, oxygen was removed by addition of 15 mg of sodium hydrosulfite in advance) was mixed with 2-(3-carboxymethyl-4-iodophenyl)propionic acid (prepared in Example 12, 40.7 mg, 0.122 mmol.) and thiosalicylic acid (37.3 mg, 0.242 mmol.). The resulting mixture was heated for 20 hours under reflux (temperature: approx. 100° C.) after addition of 10 mg of powdery copper. The reaction mixture was cooled, made acidic by addition of hydrochloric acid, and extracted with ethyl acetate. The ethyl acetate portion was washed with an aqueous sodium chloride solution, dried over magnesium sulfate, and concentrated to leave a residue. The residue was subjected to silica gel column chromatography (Wako Gel C-200, Wako Jyunyaku Industry Co., Ltd., hexane/ethyl acetate/acetic acid=7/3/1, v/v/v) to obtain 40.6 mg (0.084 mmol., yield: 69%) of the desired compound.

What is claimed is:

1. A process for preparing 2-(10,11-dihydro-10-oxodibenzo [b,f] thiepin-2-yl)propionic acid which comprises subjecting 2-(4-amino-3-carboxymethylphenyl) propionic acid or its salt to diazotization and subsequent reaction with thiophenol to produce 2-(3-carboxymethyl-4-phenylthiophenyl)propionic acid or its salt, and subjecting the product to cyclization reaction.

2. A process for preparing 2-(10,11-dihydro-10-oxodibenzo [b,f] thiepin-2-yl)propionic acid which comprises subjecting 2-(4-amino-3-carboxymethylphenyl) propionic acid or its salt to diazotization and subsequent reaction with a halogenating agent to produce 2-(3-carboxymethyl-4-halogenophenyl)propionic acid or its salt, causing a reaction of the product with thiophenol to produce 2-(3-carboxymethyl-4-phenylthiophenyl)propionic acid or its salt, and subjecting the product to cyclization reaction.

3. A process for preparing 2-(10,11-dihydro-10-oxodibenzo [b,f] thiepin-2-yl)propionic acid which comprises subjecting 2-(4-amino-3-carboxymethylphenyl) propionic acid or its salt to diazotization and subsequent reaction with thiosalicylic acid to produce 2-[3- carboxymethyl-4-(2-carboxyphenylthio)phenyl]propionic acid or its salt, esterifying the product to give a 2-[3-(lower)alkoxycarbonylmethyl-4-(2-(lower)alkoxycarbonylphenylthio)phenyl]-propionic acid (lower)alkyl ester, cyclizing the resulting ester to produce a 2-(10,11-dihydro-11-(lower)alkoxycarbonyl-10-oxodibenzo [b,f] thiepin-2-yl)propionic acid (lower)alkyl ester, and subjecting the resulting ester to hydrolysis and decarboxylation.

4. A process for preparing 2-(10,11-dihydro-10-oxodibenzo [b,f] thiepin-2-yl)propionic acid which comprises subjecting 2-(4-amino-3-carboxymethylphenyl) propionic acid or its salt to diazotization and subsequent reaction with a halogenating agent to produce 2-(3-carboxymethyl-4-halogenophenyl)propionic acid or its salt, causing a reaction of the product with thiosalicylic acid to produce 2-[3-carboxymethyl-4-(2-carboxyphenylthio) phenyl]-propionic acid or its salt, esterifying the product to give a 2-[3-(lower)alkoxycarbonylmethyl-4-(2-(lower)alkoxycarbonylphenylthio)phenyl]propionic acid (lower)-alkyl ester, cyclizing the resulting ester to produce a 2-(10,11-dihydro-11-(lower)alkoxycarbonyl-10-oxodibenzo [b,f] thiepin-2-yl)propionic acid (lower)alkyl ester, and subjecting the resulting ester to hydrolysis and decarboxylation.

5. The process according to any one of claims 1 to 4, in which the 2-(4-amino-3-carboxymethylphenyl)propionic acid or its salt is produced by reducing 2-(3-carboxymethyl-4-nitrophenyl)propionic acid or its salt.

6. The process according to any one of claims 1 to 4, in which the 2-(4-amino-3-carboxymethylphenyl)propionic acid or its salt is produced by subjecting a methylmalonic acid derivative of the following formula (A):

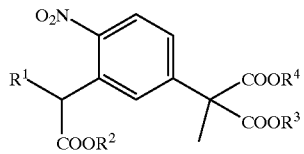

in which $R^1$ represents cyano, carboxyl, carbamoyl, alkylcarbonyl having 2 to 7 carbon atoms, alkoxycarbonyl having 2 to 7 carbon atoms, aryloxycarbonyl having 7 to 13 carbon atoms, or aralkyloxycarbonyl having 8 to 19 carbon atoms; and each of $R^2$, $R^3$ and $R^4$ independently represents hydrogen, alkyl having 1 to 6 carbon atoms, aryl having 6 to 12 carbon atoms, or aralkyl having 7 to 18 carbon atoms to hydrolysis and decarboxylation, to produce 2-(3-carboxymethyl-4-nitrophenyl)propionic acid or its salt, and reducing the product.

7. The process according to any one of claims 1 to 4, in which the 2-(4-amino-3-carboxymethylphenyl)propionic acid or its salt is produced by causing a reaction of an acetic acid ester derivative with a 2-(3-halogeno-4-nitrophenyl)-2-methylmalonic acid dialkyl ester, to give a methylmalonic acid derivative of the following formula (A):

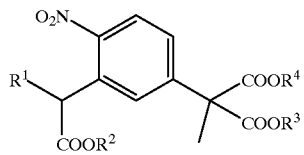

in which $R^1$ represents cyano, carboxyl, carbamoyl, alkylcarbonyl having 2 to 7 carbon atoms, alkoxycarbonyl having 2 to 7 carbon atoms, aryloxycarbonyl having 7 to 13 carbon atoms, or aralkyloxycarbonyl having 8 to 19 carbon atoms; and each of $R^2$, $R^2$ and $R^4$ independently represents hydrogen, alkyl having 1 to 6 carbon atoms, aryl having 6 to 12 carbon atoms, or aralkyl having 7 to 18 carbon atoms, subjecting the methylmalonic acid derivative to hydrolysis and decarboxylation, to produce 2-(3-carboxymethyl-4-nitrophenyl)propionic acid or its salt, and reducing the product.

8. The process according to any one of claims 1 to 4, in which the 2-(4-amino-3-carboxymethylphenyl)propionic acid or its salt is produced by causing successive reactions of a 2,4-dihalogenonitrobenzene with a methylmalonic acid diester and with an acetic acid ester derivative, to give a methylmalonic acid derivative of the following formula (A):

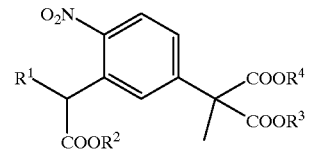

in which $R^1$ represents cyano, carboxyl, carbamoyl, alkylcarbonyl having 2 to 7 carbon atoms, alkoxycarbonyl having 2 to 7 carbon atoms, aryloxycarbonyl having 7 to 13 carbon atoms, or aralkyloxycarbonyl having 8 to 19 carbon atoms; and each of $R^2$, $R^3$ and $R^4$ independently represents hydrogen, alkyl having 1 to 6 carbon atoms, aryl having 6 to 12 carbon atoms, or aralkyl having 7 to 18 carbon atoms, subjecting the methylmalonic acid derivative to hydrolysis and decarboxylation, to produce 2-(3-carboxymethyl-4-nitrophenyl)propionic acid or its salt, and reducing the product.

9. The process according to any one of claims 1 to 4, in which the 2-(4-amino-3-carboxymethylphenyl)propionic acid or its salt is produced by reducing a methylmalonic acid derivative of the following formula (A):

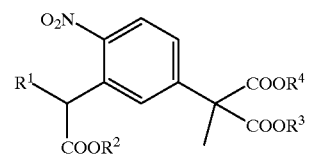

in which $R^1$ represents cyano, carboxyl, carbamoyl, alkylcarbonyl having 2 to 7 carbon atoms, alkoxycarbonyl having 2 to 7 carbon atoms, aryloxycarbonyl having 7 to 13 carbon atoms, or aralkyloxycarbonyl having 8 to 19 carbon atoms; and each of $R^2$, $R^3$ and $R^4$ independently represents hydrogen, alkyl having 1 to 6 carbon atoms, aryl having 6 to 12 carbon atoms, or aralkyl having 7 to 18 carbon atoms, to give another methylmalonic acid derivative having the following formula (B):

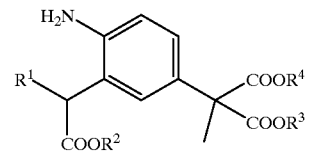

in which each of $R^1$, $R^2$, $R^3$ and $R^4$ has the meaning as defined above, and subjecting the methylmalonic acid derivative of the formula (B) to hydrolysis and decarboxylation.

10. A process for preparing 2-(10,11-dihydro-10-oxodibenzo [b,f] thiepin-2-yl)propionic acid which comprises causing a reaction of 2-(3-carboxymethyl-4-halogenophenyl)propionic acid or its salt with thiophenol, to produce 2-(3-carboxymethyl-4-phenylthiophenyl)propionic acid or its salt, and cyclizing the product.

11. A process for preparing 2-(10,11-dihydro-10-oxodibenzo [b,f] thiepin-2-yl)propionic acid which comprises causing a reaction of 2-(3-carboxymethyl-4-halogenophenyl)propionic acid or its salt with thiosalicylic acid, to produce 2-[3-carboxymethyl-4-(2-carboxyphenylthio)phenyl]propionic acid or its salt, esterifying the product to give a 2-[3-(lower)alkoxycarbonylmethyl-4-(2-(lower)alkoxycarbonylphenylthio)phenyl]propionic acid (lower) alkyl ester, cyclizing the resulting ester, and subjecting the cyclized ester to hydrolysis and decarboxylation.

12. A compound having the following formula (C):

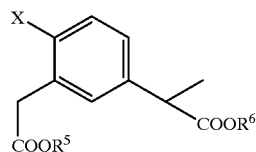

in which X represents $NO_2$, $NH_2$, halogen, or a group of the following formula:

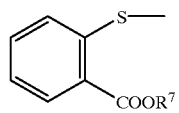

in which $R^7$ represents hydrogen, alkyl having 1 to 6 carbon atoms, aryl having 6 to 12 carbon atoms, or aralkyl having 7 to 18 carbon atoms, and each of $R^5$ and $R^6$ independently represents hydrogen, alkyl having 1 to 6 carbon atoms, aryl having 6 to 12 carbon atoms, or aralkyl having 7 to 18 carbon atoms.

13. A compound having the following formula (D):

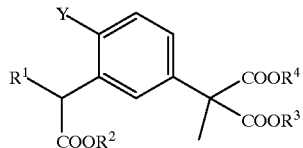

in which Y represents $NO_2$ or $NH_2$, $R^1$ represents cyano, carboxyl, carbamoyl, alkylcarbonyl having 2 to 7 carbon atoms, alkoxycarbonyl having 2 to 7 carbon atoms, aryloxycarbonyl having 7 to 13 carbon atoms, or aralkyloxycarbonyl having 8 to 19 carbon atoms; and each of $R^2$, $R^3$ and $R^4$ independently represents hydrogen, alkyl having 1 to 6 carbon atoms, aryl having 6 to 12 carbon atoms, or aralkyl having 7 to 18 carbon atoms.

14. A compound having the following formula (E):

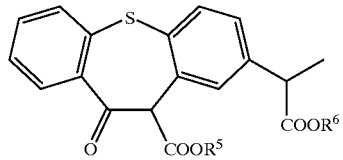

in which each of $R^5$ and $R^6$ independently represents hydrogen, alkyl having 1 to 6 carbon atoms, aryl having 6 to 12 carbon atoms, or aralkyl having 7 to 18 carbon atoms.

15. 2-(3-Carboxymethyl-4-nitrophenyl)propionic acid, its alkyl ester in which the alkyl has 1 to 6 carbon atoms, or its salt, which is according to claim 12.

16. 2-(4-Amino-3-carboxymethylphenyl)propionic acid, its alkyl ester in which the alkyl has 1 to 6 carbon atoms, or its salt, which is according to claim 12.

17. 2-[3-Carboxymethyl-4-(2-carboxyphenylthio)phenyl] propionic acid, its alkyl ester in which the alkyl has of 1 to 6 carbon atoms, or its salt, which is according to claim 12.

18. 2-(3-Carboxymethyl-4-halogenophenyl)propionic acid, its alkyl ester in which the alkyl has 1 to 6 carbon atoms, or its salt, which is according to claim 12.

19. An alkyl ester of 2-[3-alkoxycarbonylmethyl-4-(2-alkoxycarbonylphenylthio)phenyl]propionic acid in which the alkyl has 1 to 6 carbon atoms and the alkoxy has 1 to 6 carbon atoms, which is according to claim 12.

20. Dialkyl ester of 2-[3-bis(alkoxycarbonyl)-methyl-4-nitrophenyl]-2-methylmalonic acid in which the alkyl has 1 to 6 carbon atoms and the alkoxy has 1 to 6 carbon atoms, which is according to claim 13.

21. Dialkyl ester of 2-[3-[(alkoxycarbonyl)cyanomethyl]-4-nitrophenyl]-2-methylmalonic acid in which the alkyl has 1 to 6 carbon atoms and the alkoxy has 1 to 6 carbon atoms, which is according to claim 13.

22. Dialkyl ester of 2-[3-[acetyl(alkoxycarbonyl)-methyl]-4-nitrophenyl]-2-methylmalonic acid in which the alkyl has 1 to 6 carbon atoms and the alkoxy has 1 to 6 carbon atoms, which is according to claim 13.

23. Dialkyl ester of 2-[4-amino-3-bis(alkoxycarbonyl) methylphenyl]-2-methylmalonic acid in which the alkyl has 1 to 6 carbon atoms and the alkoxy has 1 to 6 carbon atoms, which is according to claim 13.

24. An alkyl ester of 2-(11-alkoxycarbonyl-10,11-dihydro-10-oxodibenzo [b,f] thiepin-2-yl)propionic acid in which the alkyl has 1 to 6 carbon atoms and the alkoxy has 1 to 6 carbon atoms, which is according to claim 14.

* * * * *